United States Patent

Garner et al.

[11] 4,072,690
[45] Feb. 7, 1978

[54] INDOLYL METHYLENE LEUCO DYESTUFFS

[75] Inventors: Robert Garner, Bury; John Barry Henshall, Manchester, both of England; Jean-Claude Petitpierre, Kaiseraugst, Switzerland

[73] Assignee: Ciba-Geigy Corporation, Ardsley, N.Y.

[21] Appl. No.: 543,581

[22] Filed: Jan. 23, 1975

[30] Foreign Application Priority Data

Feb. 1, 1974 United Kingdom ............... 4687/74

[51] Int. Cl.² ............... C07D 209/20; C07D 403/10; C07D 403/14
[52] U.S. Cl. ............... 260/326.14 R; 548/374; 548/364; 548/358; 106/14.5; 106/21; 106/22; 260/288 R; 260/296 B; 260/304 R; 260/308 B; 260/308 R; 260/310 A; 260/310 R; 260/315; 260/326.12 R; 260/326.15; 542/469; 544/102; 544/37; 544/35
[58] Field of Search ...... 260/326.15, 296 B, 326.14 R, 260/326.15

[56] References Cited

U.S. PATENT DOCUMENTS 3,527,517  9/70  Hackman ........................... 260/326.15

PUBLICATIONS

Scott, "Chem. Abstracts", vol. 62 p. 517 h (1965).
Treibs et al., "Tetrahedron Supp.,", No. 8, pt. 1. pp. 165–170 (1966) referred to in Chem. Abstracts 1967–1971 Subject Index, p. 15839 and Chem. Abstracts, vol. 66, p. 7964, #85220g.

*Primary Examiner*—Ethel G. Love
*Attorney, Agent, or Firm*—Edward McC. Roberts; Prabodh I. Almaula

[57] ABSTRACT

Indolyl methylene leuco dyestuffs of the formula

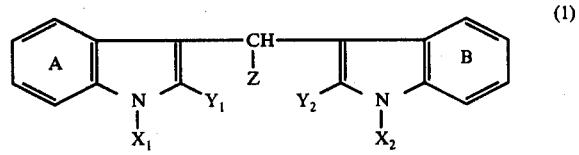

(1)

wherein $X_1$ and $X_2$ independently of the other, represent alkyl with 2 to 12 carbon atoms, alkenyl with at most 12 carbon atoms or phenylalkyl with 1 to 4 carbon atoms in the alkyl part, $Y_1$ and $Y_2$ independently of the other, represent hydrogen, alkyl with 1 to 12 carbon atoms or phenyl, Z represents alkyl with 1 to 12 carbon atoms, alkenyl with at most 12 carbon atoms, aryl, aralkyl or a heterocyclic residue and the rings A and B may be further substituted by cyano, nitro, halogen, alkyl having 1 to 4 carbon atoms, alkoxy having 1 to 4 carbon atoms or acyl with 1 to 8 carbon atoms, said methylene compounds are particularly useful as slow developing color formers in pressure-sensitive recording material and exhibit good light and air stability.

8 Claims, No Drawings

INDOLYL METHYLENE LEUCO DYESTUFFS

The present invention provides novel slow developing chromogenic compounds which are normally colourless or only weakly coloured but which yield intense colours when contacted with an electron-accepting co-reactant. The invention also relates to the manufacture of the novel compounds which may be used as colour formers in pressure-sensitive or thermoreactive recording material.

The classical combination of chromogenic compounds used in pressure-sensitive copying systems is a mixture of Crystal Violet Lactone and Benzoyl Leuco Methylene Blue. The Crystal Violet Lactone is responsible for providing the initial image which, however, is very unstable to light and moisture. This defect is overcome by the use of Benzoyl Leuco Methylene Blue which develops slowly by initiation with light, providing a greenish-blue image to replace that of the fading Crystal Violet Lactone and which is extremely light stable. However, this image suffers the disadvantages of being rather green in tone, lacking in contrast and hence not very efficient when a multiple series of copies are required. It is also not copyable by means of the commercially available reprographic machines.

It is the object of this invention to provide a further range of slow developing chromogenic compounds which exhibit good light and air stability and may be used as colour formers in formulations involving a very wide selection of instant developing chromogenes now available.

This is provided by a series of indolyl methylene compounds having the formula

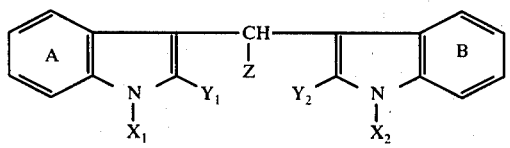

(1)

wherein $X_1$ and $X_2$ independently of the other, represent alkyl with 2 to 12 carbon atoms, alkenyl with at most 12 carbon atoms or phenylalkyl with 1 to 4 carbon atoms in the alkyl part, $Y_1$ and $Y_2$ independently of the other represent hydrogen, alkyl with 1 to 12 carbon atoms or phenyl, Z represents alkyl with 1 to 12 carbon atoms, alkenyl with at most 12 carbon atoms, aryl, aralkyl or an heterocyclic residue and the rings A and B may be further substituted by cyano, nitro, halogen, alkyl having 1 to 4 carbon atoms, alkoxy having 1 to 4 carbon atoms or acyl with 1 to 8 carbon atoms.

Of the indolyl methylene compounds of formula (1), those in which both indolyl moieties are identical are preferred.

When the radicals $X_1$, $X_2$, $Y_1$ and $Y_2$ represent alkyl, they may be straight or branched chain alkyl groups. Examples of said alkyl groups are methyl, ethyl, n-propyl, isopropyl, n-butyl, sec-butyl, hexyl, octyl or dodecyl. Alkenyl in $X_1$ and $X_2$ stands e.g. for allyl, 2-methallyl, 2-ethylallyl, 2-butenyl or octenyl. Phenylalkyl in the meanings of the X-radicals may be phenylethyl or preferably benzyl. $X_1$ and $X_2$ are preferably ethyl, octyl and benzyl, whereas preferred $Y_1$ and $Y_2$ radicals are methyl, ethyl and phenyl.

As an alkyl or alkenyl radical Z may have the same meanings as given for the X- and Y-radicals, either of which is preferably substituted by an aryl radical e.g. phenyl to form thus an aralkyl group having preferably 1 to 4 carbon atoms in the aliphatic moiety such as benzyl, piperonyl or styryl groups.

The aryl radical in the meaning of Z may be phenyl, diphenyl or naphthyl. These aromatic carbocyles can contain halogen, cyano, nitro, alkyl and/or alkoxy each having 1 to 4 carbon atoms, methylene-dioxy or acyl with 1 to 8 carbon atoms. Among the acyl groups the alkanoyl groups containing 2 to 4 carbon atoms such as acetyl or propionyl are especially noteworthy. Examples of these aromatic radicals include phenyl, o-, m- or p-methylphenyl, o-, m- or p-methoxyphenyl, o-, m- or p-chloro-, -bromo- or -fluorophenyl, o-, m- or p-nitrophenyl, 3,4-dimethoxyphenyl, 3,4-dichlorphenyl, 3,4-methylenedioxyphenyl or naphthyl.

As heterocyclic radical, Z represents mainly a 5- or 6-membered, particularly oxygen-, sulphur- or nitrogen-containing heterocycle of aromatic character. Examples of said heterocycles include thienyl, furyl, pyrrolyl, pyrazolyl, pyrazolonyl, triazolyl, pyridyl, thiazinyl or oxazinyl. In this respect, Z may also represent a radical derived from polynuclear condensed heterocycles, these preferably contain a fused benzene or naphthalene ring such as optionally substituted benzothiophen, indole, indazole, benzothiazole, benzotriazole, naphthotriazole, quinoline, carbazole, phenothiazine or phenoxazine.

These mono- or polynuclear heterocyclic radicals can contain the substituents of the type listed above, particularly halogens, cyano, nitro, alkyl having 1 to 4 carbon atoms, alkoxy having 1 to 4 carbon atoms, acyl having 1 to 8 carbon atoms, or phenyl.

The preferred heterocyclic radicals represented by Z are 2-furyl, 2-thienyl, 4-pyridyl, 3-indolyl and 2-(N-methylpyrrolyl) or 1-acetyl-indol-3-yl.

As preferred substituents, the benzene rings A and B may contain halogens, nitro, methyl or methoxy. Preferably, they are not further substituted.

Halogen, in each occurrence in the definition of the substituents listed above, preferably stands for fluorine, bromine or especially chlorine.

Practically important groups of the compounds of the formula (1) may be defined by the following formula

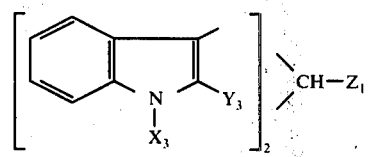

wherein $X_3$ represents alkyl with 2 to 12 carbon atoms or benzyl, $Y_3$ represents hydrogen, methyl, ethyl or phenyl, $Z_1$ represents an aralkyl radical selected from benzyl, piperonyl and styryl, an aryl radical selected from phenyl, diphenyl or naphthyl, said aryl radical may be substituted by halogen methylenedioxy, nitro, alkyl having 1 to 4 carbon atoms or by alkoxy having 1 to 4 carbon atoms, or a heterocyclic radical selected from furyl, thienyl, pyrrolyl, pyrazolyl, pyrazolonyl, pyridyl, thiazinyl, oxazinyl, indolyl, indazolyl, benzothienyl, benzothiazolyl, benzotriazolyl, naphthotriazolyl, quinolyl, carbazolyl, phenothiazinyl or phenoxazinyl, said mono- and polynuclear heterocycles may be substituted by halogen, cyano, nitro, alkyl with 1 to 4 carbon atoms, alkoxy with 1 to 4 carbon atoms or by phenyl.

Particularly valuable indolyl methylene compounds of the formulae (1) and (2) are those methylene compounds which are listed under A and B, respectively.

A. Indolyl methylene compounds of the formula

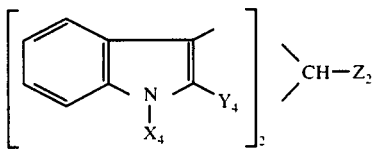
(3)

wherein $X_4$ represents alkyl with 2 to 8 carbon atoms or benzyl, $Y_4$ represents methyl or phenyl and $Z_2$ represents styryl, phenyl or naphthyl, said phenyl radical may be substituted by halogen, methylenedioxy, nitro, methyl or methoxy. Among these compounds of formula (3) $Z_2$ is particularly phenyl, methylphenyl, methoxyphenyl, nitrophenyl or styryl.

B. Indolyl methylene compounds of the formula

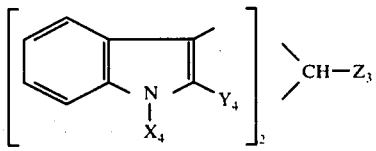
(4)

wherein $X_4$ and $Y_4$ have the given meanings and $Z_3$ represents furyl, thienyl, pyridyl, pyrrolyl or indolyl, wherein the pyrrolyl radical may be further substituted by alkyl having 1 to 4 carbon atoms and the indolyl residue may be further substituted by alkyl having 1 to 4 carbon atoms, cyano, halogen, alkoxy having 1 to 4 carbon atoms, phenyl and particularly by alkanoyl with 2 to 4 carbon atoms, especially by acetyl at the nitrogen atom.

In this case $X_4$ is most preferably ethyl, $Y_4$ is with advantage methyl and $Z_3$ represents particularly furyl, pyridyl, N-methylpyrrolyl or indolyl as well as 1-acetylindol-3-yl. These most preferred compounds falling under formula (4) as well as bis(1-ethyl-2-methylindol-3-yl)-nitrophenyl or -styryl methylene compounds falling under formula (3) are especially distinguished by their stability on exposure to light and air in the absence of an electron-accepting co-reactive substance.

The new indolyl methylene compounds of the formula (1) or of the subordinate formulae are obtained by a method known in the art. An advantageous procedure to follow is to react, simultaneously or successively, one mole of an aldehyde of the formula

Z — CHO (5)

with 1 mole each of the indole compounds of the formulae

(6)

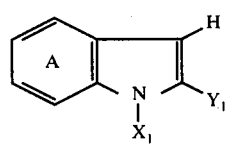

and

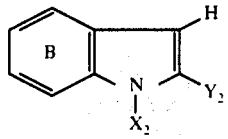
(7)

wherein A, B, $X_1$, $X_2$, $Y_1$, $Y_2$ and Z have the given meanings.

The reaction is advantageously carried out at a temperature of 20° to 150° C, preferably at 80° to 120° C and in the presence of sulphuric acid which is preferably of 70 to 98%. The reaction time is dependent upon the temperature and is typically 8 to 16 hours at 120° C. Alcohols, for example iso-propyl alcohol, may be added to the reaction mixture to assist solubility of the reagents and product, in which case the reaction temperature is between 20° C and the reflux temperature of the mixture. The use of urea is, in some cases, beneficial in accelerating the reaction time and increasing the yield. In place of sulphuric acid may be used hydrochloric acid, zinc chloride, ferric chloride, aluminium chloride, polyphosphoric acid, phosphorus oxychloride, thionyl chloride or phosphorus pentoxide. The use of acetic anhydride both as reagent and solvent is, in many cases, advantageously. In this event, when for example Z represents an N-unsubstituted indolyl residue an acetyl group is introduced at the nitrogen atom during the reaction. The reaction may also be performed in a water-insoluble solvent using catalytic quantities of an organic sulphonic acid for example, p-toluene sulphonic acid. A preferred method of manufacture for producing symmetrical compounds of formula (1) is to react 2 mols of a compound of formula (6) or (7) with 1 mole of the aldehyde of formula (5).

The new indolyl methylene compounds according to the invention are particularly useful as slow developing colour formers advantageously in combination with further chromogenic compounds when brought into close contact with an acidic co-reactant substance that is electron-accepting.

Typical co-reactants are, for example, attapulgus clay, silton clay, silica, bentonite, halloysite, aluminium oxide, aluminium phosphate, kaolin or any acidic clay, or an acid reacting polymeric material such as a phenolic polymer, an alkylphenolacetylene resin, a maleic acid-rosin resin or a partially or wholly hydrolysed polymer of maleic anhydride with styrene, ethylene, vinyl methyl ether or carboxy polymethylenes. The preferred co-reactants are attapulgus clay, silton clay, silica or a phenol-formaldehyde resin.

By varying the structure of this new range of indolyl methylene compounds certain properties may be "built-in", for example, the colour ranging from orange to pink, red, violet and green, fade stability for compatibility with other colour formers in mixtures, and any solubility characteristics which would allow greater flexibility in the choice of solvents used in microencapsulation and other modes of application.

The colour formers of the invention above all are suitable for the use in so-called pressure-sensitive recording material. Such a material e.g. includes at least one pair of sheets, which comprises at least a colour former of formula (1) and an electron accepting substance. The colour former is desirably dissolved in an organic solvent, and is preferably contained in pressure rupturable microcapsules.

The colour former, upon coming into contact with the electron accepting substance, produces a coloured marking at the points where the pressure is applied.

These colour formers which are comprised in the pressure-sensitive copying material are prevented from becoming active by being separated from the electron accepting substance. This can be done by incorporating the colour formers into a foam-, sponge- or honeycomb-like structure. Preferably however the colour formers are microencapsulated.

When the capsules are ruptured by pressure from e.g. a pencil, and the colour former solution is thus transferred into an adjacent sheet coated with a substrate capable of acting as an electron acceptor, a coloured image is produced. This new colour results from the thus produced dyestuff which absorbs in the visible region of the electromagnetic spectrum.

The general art of making microcapsules of some character has long been known. Well known methods e.g. are disclosed in U.S. Pat. Nos. 2,183,053, 2,797,201, 2,800,457, 2,800,458, 2,964,331, 3,016,308, 3,171,878, 3,265,630, 3,405,071, 3,418,250, 3,418,656, 3,424,827, and 3,427,250. Further methods are disclosed in British patent specification Nos. 989,264 and above all 1,156,725, 1,301,052 and 1,355,124. Any of these and other methods are suitable for encapsulating the present colour formers.

Preferably the present colour formers are encapsulated dissolved in organic solvents. Suitable solvents are preferably non-volatile e.g. polyhalogenated diphenyl such as trichlorodiphenyl and its mixture with liquid paraffin, tricresyl phosphate, di-n-butyl phthalate, dioctyl phthalate, trichlorobenzene, nitrobenzene, trichloroethyl-phosphate, petroleum ether, hydrocarbon oils, such as paraffin, alkylated derivatives of naphthalene or diphenyl, terphenyls, partially hydrogenated terphenyls, chlorinated or hydrogenated condensed aromatic hydrocarbons. The capsule walls can be obtained by coacervation forces evenly around the droplets of the colour former solution, wherein the encapsulating material may consist of gelatine, as e.g. described in U.S. Pat. No. 2,800,457.

Alternatively, the capsules preferably may be made of aminoplast or modified aminoplasts by polycondensation as described in British patent specification Nos. 989,264 or 1,156,725.

A preferred arrangement is wherein the encapsulated colour former is coated on the back side of a transfer sheet and the electron accepting substance is coated on the front side of a receiving sheet.

In another preferred material the new indolyl methylene compounds which generally develop slowly are coencapsulated with one or more instant developing known colour formers, such as crystal violet lactone, a bis aryl phthalide, a bis-indolyl phthalide or any substituted fluoran compound.

In this respect, it is a surprising facet of the invention, that with the new indolyl methylene compounds according to the invention it becomes possible to formulate mixtures involving pairs of instant and slow developing chromogenes with similar spectral characteristics in which all the desired properties are met, for example good light-fastness involving little or no tonal change on a prolonged exposure, together with good stability to moisture and good copyability at all stages in the lifetime of the developed image.

The microcapsules containing the colour formers of formula (1) are used for making pressure-sensitive copying material of the various types known in the art. The various systems mainly are distinguished by the arrangement of the capsules, the colour reactants and the support material.

The microcapsules may be in an undecoating of the upper sheet and the colour reactants, that is the electron acceptor and coupler, may be in the overcoating of the lower sheets. However, the components may also be used in the paper pulp.

Another arrangement we have in the self-contained papers. There the microcapsules containing the colour former and the colour reactants are in or on the same sheet as one or more individual coatings or in the paper pulp.

Such pressure-sensitive copying materials are described e.g. in U.S. Pat. Nos. 3,516,846, 2,730,457, 2,932,582, 3,427,180, 3,418,250 and 3,418,656. Further systems are disclosed in British patent specification Nos. 1,042,596, 1,042,597, 1,042,598, 1,042,599, 1,053,935 and 1,517,650. Microcapsules containing the colour formers of formula (1) are suitable for any of these and other systems.

The capsules are preferably fixed to the carrier by means of a suitable adhesive. Since paper is the preferred carrier material, these adhesives are predominantly paper coating agents, such as e.g. gum arabic, polyvinyl alcohol, hydroxymethylcellulose, casein, methylcellulose or dextrin.

In the present application, the definition "paper" not only includes normal papers from cellulose fibers, but also papers in which the cellulose fibers are replaced (partially or completely) by synthetic fibers of polymers.

Percentages in the following examples are expressed by weight, unless otherwise stated.

EXAMPLE 1

A mixture of 7 ml of acetic anhydride, 9.53 g 1-ethyl-2-methylindole and 4.68 g of 1-naphthaldehyde is heated at 110° C for 4 hours. Whilst cooling, 20 ml methanol is added and the resulting suspension is stirred for 1 hour. The solid is filtered off, washed with methanol and dried to yield 13.1 g of a leuco methylene dyestuff of the formula

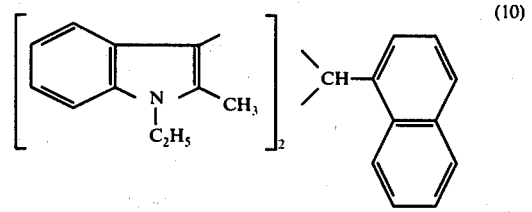

having a melting point of 199°–202° C.

When brought into contact with an acidic clay, the color former of formula (10) gives a red image (attapulgus clay $\lambda_1$ 544; silton clay $\lambda_1$ 544).

EXAMPLE 2

A mixture of 24 ml acetic anhydride, 10.6 g benzaldehyde and 31.8 g 1-ethyl-2-methylindole is stirred at 100° C for 4 hours. The reaction mixture is cooled to 60° C and 60 ml of methanol is added whereupon a solid crystallises out. The solid is filtered off, washed with methanol and dried to yield 34.8 g of a leuco methylene dyestuff of the formula

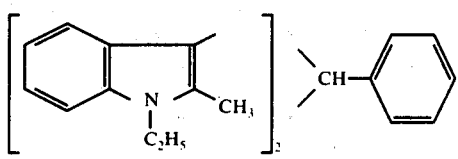

(11)

Melting point 155°–156° C.

When brought into contact with an acidic clay, the color former of formula (11) gives a red image (attapulgus clay $\lambda_1$ 543, $\lambda_2$ 400; silton clay $\lambda_1$ 540).

EXAMPLE 3

A mixture of 7 ml acetic anhydride, 4.35 g indole-3-carboxaldehyde and 9.43 g 1-ethyl-2-methylindole is heated at 110° C for 1.5 hours. Whilst cooling, 25 ml methanol is added and the solid thus obtained is filtered off and dried to yield 13.6 g of a leuco methylene dyestuff of the formula

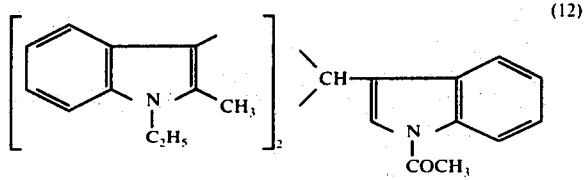

(12)

Melting point 185° C.

This bis-indolyl-methylene compound is entirely stable on exposure to light and air in the absence of an electron-accepting co-reactive substance.

When brought into contact with an acidic clay, the color former of formula (12) gives an orange image (attapulgus clay $\lambda_1$ 485; silton clay $\lambda_1$ 500).

This bis-indolyl-methylene compounds of the formula

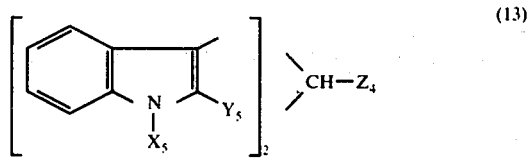

(13)

listed in the table below can be manufactured similarly. When contacted with an acidic clay such as attapulgus clay and silton clay the compounds of formula (13) give the colours indicated in the Table.

Table

| Ex. No. | $X_5$ | $Y_5$ | $Z_4$ | m.p.° C | Attapulgus Clay Colour | $\lambda_1$ | $\lambda_2$ | Silton Clay Colour | $\lambda_1$ | $\lambda_2$ |
|---|---|---|---|---|---|---|---|---|---|---|
| 4 | —C$_3$H$_7$ | (phenyl) | (phenyl) | 148–149 | green | 405 | 604 | green | 418 | 602 |
| 5 | —C$_8$H$_{17}$ | —CH$_3$ | (phenyl) | oil | red | 546 | 400 | red | 546 | 400 |
| 6 | —CH$_2$—(phenyl) | —CH$_3$ | (phenyl) | 150–152 | red | 548 | 404 | red | 542 | 410 |
| 7 | —C$_2$H$_5$ | —CH$_3$ | o-CH$_3$-phenyl | 140–141 | red | 537 | — | red | 535 | — |
| 8 | —C$_2$H$_5$ | —CH$_3$ | m-CH$_3$-phenyl | 132–133 | red | 541 | — | red | 543 | — |
| 9 | —C$_2$H$_5$ | —CH$_3$ | p-CH$_3$-phenyl | 188–191 | red | 544 | 405 | red | 540 | 410 |
| 10 | —C$_2$H$_5$ | —CH$_3$ | p-CH$_3$O-phenyl | 130–131 | red | 542 | — | red | 540 | — |

Table-continued

| Ex. No. | $X_5$ | $Y_5$ | $Z_4$ | m.p.° C | Attapulgus Clay Colour | $\lambda_1$ | $\lambda_2$ | Silton Clay Colour | $\lambda_1$ | $\lambda_2$ |
|---|---|---|---|---|---|---|---|---|---|---|
| 11 | $-C_2H_5$ | $-CH_3$ | 3-OCH₃-phenyl | 125–126 | red | 540 | — | red | 540 | — |
| 12 | $-C_2H_5$ | $-CH_3$ | 4-OCH₃-phenyl | 177–178 | orange | 540 | 436 | orange | 536 | 444 |
| 13 | $-C_2H_5$ | $-CH_3$ | 4-F-phenyl | 143 | red | 548 | — | red | 550 | — |
| 14 | $-C_2H_5$ | $-CH_3$ | 4-Cl-phenyl | 188–189 | pink | 534 | 400 | pink | 532 | 404 |
| 15 | $-C_2H_5$ | $-CH_3$ | 4-Br-phenyl | 205–206 | red | 548 | 400 | red | 550 | 405 |
| 16 | $-C_6H_{13}$ | $-H$ | phenyl | 73–74 | pink | 529 | 397 | pink | 528 | — |
| 17 | $-C_2H_5$ | $-CH_3$ | 3-NO₂-phenyl | 179–180 | violet | 558 | — | violet | 558 | — |
| 18 | $-C_2H_5$ | $-CH_3$ | 2-NO₂-phenyl | 222–223 | orange | 544 | — | orange | 496 | — |
| 19 | $-C_2H_5$ | $-CH_3$ | 4-NO₂-phenyl | 132–133 | violet | 560 | — | violet | 500 | — |
| 20 | $-C_2H_5$ | $-CH_3$ | 2,3-(OCH₃)₂-phenyl | 77–80 | red | 536 | — | orange | 485 | — |
| 21 | $-C_2H_5$ | $-CH_3$ | 2,3-Cl₂-phenyl | 142–144 | violet | 555 | — | violet | 560 | — |
| 22 | $-C_2H_5$ | $-CH_3$ | $-CH=CH-$phenyl | 124 | violet | 542 | — | violet | 500 | — |
| 23 | $-C_2H_5$ | $-CH_3$ | 2-thienyl | 163–164 | red | 553 | 445 | orange | 550 | 448 |
| 24 | $-C_2H_5$ | $-CH_3$ | 1-methyl-2-pyrrolyl | 194–197 | orange | 490 | — | orange | 490 | — |

Table-continued

| Ex. No. | $X_5$ | $Y_5$ | $Z_4$ | m.p. °C | Attapulgus Clay Colour | $\lambda_1$ | $\lambda_2$ | Silton Clay Colour | $\lambda_1$ | $\lambda_2$ |
|---|---|---|---|---|---|---|---|---|---|---|
| 25 | $-C_2H_5$ | $-CH_3$ | 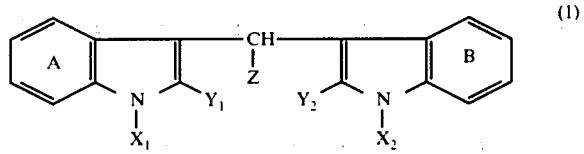 | 176–178 | red | 542 | 465 | red | 540 | 490 |
| 26 | $-C_2H_5$ | $-CH_3$ | 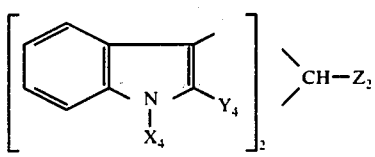 | 110 | violet | 562 | — | violet | 564 | — |

We claim:

1. An indolyl methylene compound of the formula

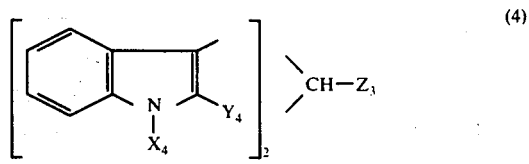 (1)

wherein $X_3$ represents alkyl with 2 to 12 carbon atoms or benzyl, $Y_3$ represents hydrogen, methyl, ethyl or phenyl, $Z_1$ represents an aralkyl radical selected from benzyl and styryl, an aryl radical selected from phenyl, diphenyl or naphthyl which is unsubstituted or substituted by halogen, methylenedioxy, nitro, alkyl having 1 to 4 carbon atoms or by alkoxy having 1 to 4 carbon atoms, or indolyl unsubstituted or substituted by halogen, cyano, nitro, alkyl with 1 to 4 carbon atoms, alkoxy with 1 to 4 carbon atoms, alkanoyl with 2 to 4 carbon atoms or phenyl.

2. An indolyl methylene compound according to claim 3 of the formula $$\left[ \begin{array}{c} \includegraphics \\ N \\ | \\ X_4 \end{array} Y_4 \right]_2 \!\!\! \diagup\!\!\! CH-Z_2 \quad (3)$$

wherein $X_4$ represents alkyl with 2 to 8 carbon atoms or benzyl, $Y_4$ represents methyl or phenyl and $Z_2$ represents styryl, phenyl, or naphthyl, said phenyl radical is unsubstituted or substituted by halogen, methylenedioxy, nitro, methyl or methoxy.

3. An indolyl methylene compound according to claim 2, wherein $Z_2$ represents phenyl, methylphenyl, methoxyphenyl, nitrophenyl or styryl.

4. An indolyl methylene compound according to claim 1 of the formula $$\left[ \begin{array}{c} \includegraphics \\ N \\ | \\ X_4 \end{array} Y_4 \right]_2 \!\!\! \diagup\!\!\! CH-Z_3 \quad (4)$$

wherein $X_4$ represents alkyl with 2 to 8 carbon atoms or benzyl, $Y_4$ represents methyl or phenyl, and $Z_3$ represents indolyl, unsubstituted or substituted by cyano, halogen, alkyl having 1 to 4 carbon atoms, alkoxy having 1 to 4 carbon atoms, alkanoyl with 2 to 4 carbon atoms or phenyl.

5. An indolyl methylene compound according to claim 4, wherein $X_4$ is ethyl, $Y_4$ is methyl and $Z_3$ represents indolyl.

6. An indolyl methylene compound according to claim 2, wherein $X_4$ is ethyl, $Y_4$ is methyl and $Z_3$ is phenyl.

7. An indolyl methylene compound according to claim 2, wherein $X_4$ is ethyl, $Y_4$ is methyl and $Z_3$ is methoxyphenyl.

8. An indolyl methylene compound according to claim 4, wherein $X_4$ is ethyl, $Y_4$ is methyl and $Z_3$ is 1-acetylindol-3-yl.

* * * * *

UNITED STATES PATENT AND TRADEMARK OFFICE
CERTIFICATE OF CORRECTION

PATENT NO. : 4,072,690
DATED : February 7, 1978
INVENTOR(S) : Robert Garner et al It is certified that error appears in the above-identified patent and that said Letters Patent are hereby corrected as shown below:

Claim 1, column 11, line 20,

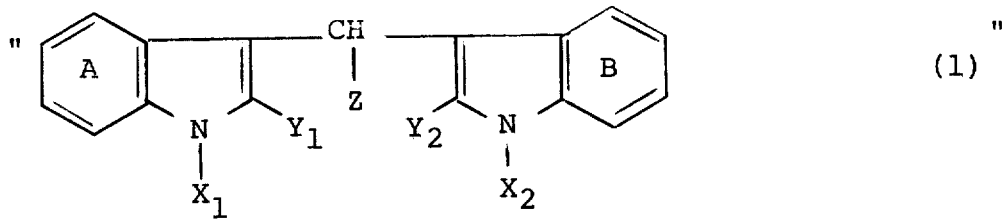

(1)

UNITED STATES PATENT AND TRADEMARK OFFICE
CERTIFICATE OF CORRECTION

PATENT NO. : 4,072,690
DATED : February 7, 1978
INVENTOR(S) : Robert Garner et al Page 2 of 2

It is certified that error appears in the above-identified patent and that said Letters Patent are hereby corrected as shown below:

should be -- 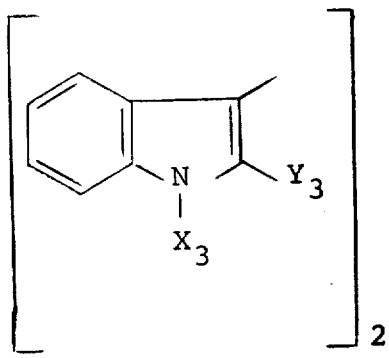 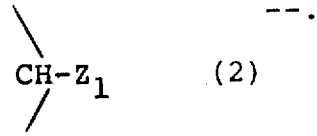 (2) --.

Signed and Sealed this

First Day of April 1980

[SEAL]

Attest:

SIDNEY A. DIAMOND

Attesting Officer

Commissioner of Patents and Trademarks